United States Patent [19]

Wang et al.

[11] Patent Number: 4,579,893
[45] Date of Patent: Apr. 1, 1986

[54] BENZOXAZOLE STABILIZER COMPOUNDS AND POLYMERIC MATERIALS STABILIZED THEREWITH

[75] Inventors: Richard H. S. Wang, Kingsport, Tenn.; Michael Bellas, Wigan, England; William W. Blount, Jr., Surgoinsville, Tenn.

[73] Assignee: Eastman Kodak Company, Rochester, N.Y.

[21] Appl. No.: 568,569

[22] Filed: Jan. 6, 1984

[51] Int. Cl.⁴ .............................................. C08K 5/35
[52] U.S. Cl. ...................................... 524/87; 524/90; 524/556; 524/560; 524/590; 524/601; 524/604; 524/605; 548/217
[58] Field of Search .................. 524/87, 90, 601, 604, 524/605, 590, 556, 560; 548/217

[56] References Cited

U.S. PATENT DOCUMENTS

| | | | |
|---|---|---|---|
| 3,244,526 | 4/1966 | Copeland | 548/217 |
| 3,674,781 | 7/1972 | Schinzel et al. | 548/217 |
| 4,096,115 | 6/1978 | Irick, Jr. et al. | 524/87 |
| 4,201,713 | 5/1980 | Harnisch | 548/217 |
| 4,220,760 | 9/1980 | Erckel et al. | 548/217 |
| 4,282,355 | 8/1981 | Erckel et al. | 548/217 |
| 4,308,194 | 12/1981 | Irick, Jr. et al. | 524/87 |

Primary Examiner—Lester L. Lee
Attorney, Agent, or Firm—J. Frederick Thomsen; D. B. Reece, III

[57] ABSTRACT

Disclosed are compounds having the formula

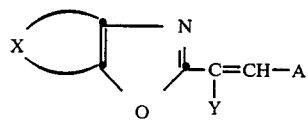

wherein
X is the residue of a benzoxazole radical;
Y is carboxyl, alkoxycarbonyl, alkanoyl, cyano, carbamoyl, N-alkylcarbamoyl or N,N-dialkylcarbamoyl; and
A is phenyl, naphthyl or phenyl or napthyl substituted with one or more substituents selected from hydroxy, halogen, alkyl, alkoxy, cycloalkyl, aryl, aryloxy or Y. Also disclosed are polymeric materials stabilized against degradation by ultraviolet light by the incorporation therein of one or more of the above-defined compounds.

10 Claims, No Drawings

BENZOXAZOLE STABILIZER COMPOUNDS AND POLYMERIC MATERIALS STABILIZED THEREWITH

This invention relates to certain novel benzoxazole compounds and to certain polymeric materials containing the compounds which inhibit the degradation of such polymeric materials normally caused by exposure to ultraviolet light.

The novel compounds of our invention have the general formula

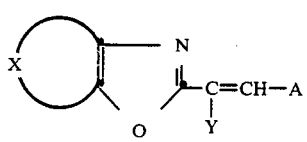

wherein

X is the residue of a benzoxazole radical;
Y is carboxyl, alkoxycarbonyl, alkanoyl, cyano, carbamoyl, N-alkylcarbamoyl or N,N-dialkylcarbamoyl; and
A is phenyl, naphthyl or phenyl or naphthyl substituted with one or more substituents selected from hydroxy, halogen, alkyl, alkoxy, cycloalkyl, aryl, aryloxy or Y.

The residue represented by X may be unsubstituted, i.e. a butadiendiyl group, or substituted for example with up to three substituents such as the groups represented by Y or those which may be present on the substituted phenyl groups which A may represent. A preferred group of benzoxazoles containing residue X has the structure

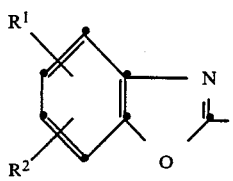

wherein $R^1$ is hydrogen, alkyl, alkoxy or halogen and $R^2$ is an $R^1$ substituent, carboxyl or alkoxycarbonyl.

The phenyl radical represented by A preferably has the structure

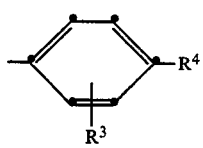

wherein $R^3$ and $R^4$ are independently selected from hydrogen, alkyl, alkoxy, hydroxy, halogen, cycloalkyl, aryl or aryloxy. The alkyl groups and the alkyl moiety of the alkoxy, alkoxycarbonyl and alkanoyl groups set forth in the preceding definitions may contain up to about 12 carbon atoms although the carbon content of such groups normally will not exceed six carbon atoms. These alkyl groups and moieties may be unsubstituted or substituted with substituents such as alkoxy, hydroxy, halogen, etc. Bromine and, especially, chlorine are typical halogen substituents. Cyclohexyl and alkyl-substituted cyclohexyl are examples of the cyclohexyl groups which $R^1$ and/or $R^2$ may represent. Examples of the aryl groups and aryl moiety of the aryloxy groups specified in the above definitions include phenyl and phenyl substituted with one or two of the substituents which $R^2$ and Y can represent.

A group of our novel compounds which, because of their cost:effectiveness ratio, is particularly preferred has the formula

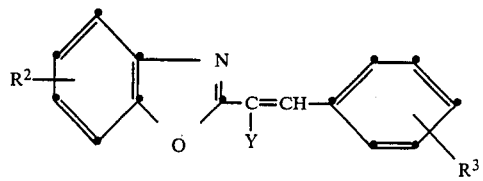

wherein $R^2$ is hydrogen, alkyl, alkoxy, chlorine, carboxyl or alkoxycarbonyl;
Y is alkoxycarbonyl or cyano; and
$R^3$ is ortho or para hydroxy or alkoxy.

Our novel benzoxazole compounds may be prepared according to known procedures by reacting a benzaldehyde having the formula OHC—A with a 2-substituted-methylbenzoxazole of the formula

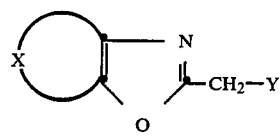

in the presence of a base and an inert solvent. The 2-substituted-methylbenzoxazoles also may be prepared according to published techniques. For example, a nitrile having the formula NCCH$_2$—Y may be treated with hydrogen chloride and an alkanol such as ethanol to give an imino ether hydrochloride which is then reacted with an o-aminophenol to given the benzoxazole compound, e.g.

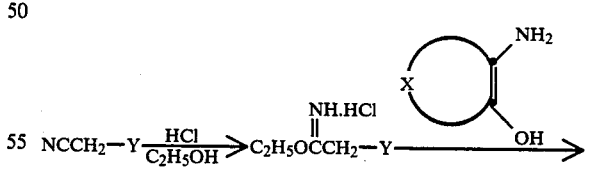

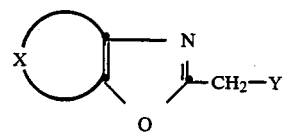

Alternatively, the benzoxazole intermediates may be prepared by reacting a substituted acetic acid or derivative thereof with an o-aminophenol in the presence of an acid and an inert solvent, e.g.

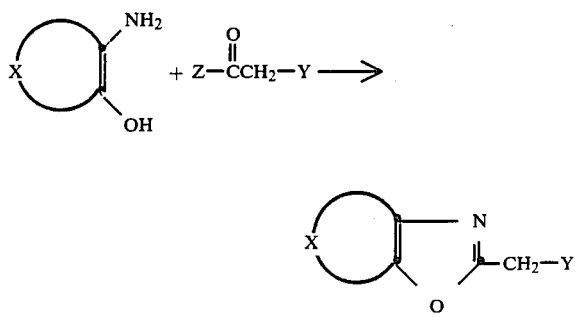

wherein Z is hydroxyl, alkoxy, aryloxy, etc.

The preparation of the novel compounds of this invention is further illustrated by the following examples.

EXAMPLES 1-19

Anhydrous hydrogen chloride (2.0 mol) is added to a mixture of ethyl cyanoacetate (1.0 mol) and ethanol (1.1 mol) in ethyl acetate (1 L) at 0° C. over a period of three hours. The mixture is then stirred at 5°–10° C. for ten additional hours. Removal of the solvent under reduced pressure gives the intermediate ethyl 3-ethoxy-3-iminopropanoate hydrochloride in a yield of about 90%. The appropriate o-aminophenol (1.0 mol) is added with vigorous stirring below 15° C. to a solution of ethyl 3-ethoxy-3-iminopropanoate hydrochloride (1.0 mol) in methanol and allowed to react for ten hours at less than 20° C. After removal of the methanol, the residue is extracted with acetone and the extract is concentrated and diluted with cold 2-propanol to precipitate the ethyl 2-benzoxazolylacetate intermediate (m.p. 50°–53° C.) which is collected by filtration in a yield of 85%. A mixture of the ethyl 2-benzoxazolylacetate (1.0 mol), a benzaldehyde compound (1.0 mol), piperidine (10 ml) and acetic acid (2.5 ml) in toluene (1 L) is refluxed with agitation for four hours while removing the water of reaction. The reaction mixture is then cooled and filtered to obtain the product. This general procedure may be used to prepare the following compounds:

Example 1 Ethyl 2-(2-benzoxazolyl)-3-(4-methoxyphenyl)propenoate
Example 2 Ethyl 2-(2-benzoxazolyl)-3-(4-hydroxyphenyl)propenoate
Example 3 Ethyl 2-(5-chloro-2-benzoxazolyl)-3-(4-methoxyphenyl)propenoate
Example 4 Ethyl 2-(2-benzoxazolyl)-3-[4-(2-hydroxyethoxy)phenyl]propenoate
Example 5 Ethyl 2-[5,7-bis(1,1-dimethylpropyl)-2-benzoxazolyl]-3-(4-methoxyphenyl)-propenoate
Example 6 Ethyl 2-(6-ethoxycarbonyl-2-benzoxazolyl)-3-(4-methoxyphenyl)propenoate
Example 7 Ethyl 2-(5-ethoxycarbonyl-2-benzoxazolyl)-3-(4-butoxyphenyl)propenoate
Example 8 Methyl 2-(6-methoxy-2-benzoxazolyl)-3-(4-methoxyphenyl)propenoate
Example 9 Ethyl 2-(2-benzoxazolyl)-3-[3,5-bis-(1,1-dimethylethyl)-4-hydroxyphenyl]propenoate
Example 10 Ethyl 2-(2-benzoxazolyl)-3-(2-methoxyphenyl)propenoate
Example 11 Ethyl 2-(2-benzoxazolyl)-3-(2,4-dimethoxyphenyl)propenoate
Example 12 Ethyl 2-(2-benzoxazolyl)-3-(3,4-dihydroxyphenyl)propenoate
Example 13 Ethyl 2-(2-benzoxazolyl)-3-(3,4,5-trimethoxyphenyl)propenoate
Example 14 2-(2-Benzoxazolyl)-3-(3-chloro-4-methoxyphenyl)acrylonitrile
Example 15 Ethyl 2-(2-benzoxazolyl)-3-(4-phenoxyphenyl)propenoate
Example 16 Ethyl 2-(2-benzoxazolyl)-3-(1-naphthyl)-propenoate
Example 17 Ethyl 2-[6-(2-hydroxyethoxy)-2-benzoxazolyl]-3-[4-(2-hydroxyethoxy)phenyl]propenoate
Example 18 3-(2-Benzoxazolyl)-4-(4-methoxyphenyl)-3-butene-2-one
Example 19 2-(2-Benzoxazolyl)-3-(4-methoxyphenyl)N,N-dimethylpropenamide The compounds of the invention are useful as stabilizers for organic materials normally degraded by prolonged exposure to ultraviolet light, i.e. actinic radiation. The heat stability and low volatility exhibited by the compounds permit their incorporation into such materials according to conventional melt blending processes. Materials which may be stabilized thus include organic polymeric materials such as synthetic, normally-solid, polymeric materials and polymer-containing compositions useful in the preparation of coating compositions and films and other shaped articles such as sheeting and molded objects.

Our novel compounds are especially suitable for the stabilization of materials comprising polymers which contain ester groups which may be present in the main chain or backbone of the polymer and/or pendant thereon. Examples of such ester-containing polymers include acrylics such as those derived from esters of acrylic and methacrylic acid; polyesters such as those obtained from one or more diols, diolethers and/or triols and one or more aliphatic, cycloaliphatic and/or aromatic dicarboxylic acids including oil modified polyesters, cellulose esters such as cellulose acetate, cellulose acetate propionate, cellulose acetate butyrate and cellulose nitrate; polyurethanes such as those derived from toluene diisocyanate or 4,4'-diisocyanatodiphenylmethane and a polyalkylene glycol; and polycarbonates such as are obtained from bisphenol-A and phosgene. These polymers may contain chemically-different ester linkages, e.g. as are present in polymeric compositions comprising a polyester cross-linked with a diisocyanate.

The benzoxazole compounds provided by this invention are most suitable for stabilizing polymeric materials comprising a polyester containing recurring phthalate, particularly terephthalate, moieties, i.e. polyesters in which the dicarboxylic acid repeating unit is derived from a phthalic acid such as terephthalic acid. Such polymeric compositions are useful as binders in automotive and powder coating compositions and in the manufacture of films, sheeting and other shaped articles.

The amount of benzoxazole compound that normally will be sufficient to inhibit significantly the degradation of organic polymeric compositions which are susceptible to the effects of ultraviolet light is at least about 0.01 weight percent based on the weight of the primary polymer present. While the optimum concentration of stabilizer compound will depend on the ultimate utility of the stabilized composition, it usually will be in the range of about 0.1 to 5.0 weight percent. Polymer-containing formulations intended for use in the preparation of coatings having a thickness of two mils or less normally should contain from about 0.5, preferably 2.0, to 5.0 weight percent stabilizer whereas compositions intended for molding shaped articles typically will contain about 0.1 to 3.0 weight percent of the stabilizer compound.

The novel stabilized compositions provided by our invention can be prepared according to well-known techniques. The stabilizer compound can be incorporated into the polymeric materials during the normal polymer processing or compounding operations, for example, by hot-milling followed by extrusion into pellets. Alternatively, the stabilizer compound may be added prior to or during the preparation of the polymeric material. For example, it may be combined with one or more of the monomers or it may be added to a prepolymer or to a low molecular weight polymer prior to the final polymerization step. The stabilizer compound also may be incorporated chemically into the polymeric material, for example, by adding a stabilizer containing reactive groups prior to or during the formation of the polymer resulting in stabilizer moieties being present in the polymer chain or pendant thereto. The stabilized compositions may contain other additives such as pigments, antioxidants, flow control agents, plasticizers, processing aids and modifiers, etc.

The effectiveness of the compounds of Examples 1, 2 and 3 as stabilizers in KODAR Copolyester PETG 6363, an amorphous, thermoplastic copolymer of 69 mole percent ethylene glycol, 31 mole percent 1,4-cyclohexanedimethanol and dimethyl terephthalate having an inherent viscosity of approximately 0.75, was determined by the following procedure:

Dry granulations of the copolyester containing either no stabilizer or 0.5 weight percent of one of the stabilizer compounds are extruded into 0.0625 inch diameter rods which are chopped into pellets and injection molded into flat bars measuring 2.5×2.5×0.0625 inches. The flat bars are exposed in an Atlas XWR Weather-Ometer (carbon arc light source) until a flatwise impact strength of six or less, as determined by ASTM Procedure D256-56, is obtained. The results obtained are shown below.

| Stabilizer Compound | Flatwise Impact Strength | | |
|---|---|---|---|
|  | Initial | 500 Hours | 1000 Hours |
| None | 15 | 2 | — |
| Example 1 | 15 | 11 | 6 |
| Example 2 | 14 | 12 | 2 |
| Example 3 | 14 | 12 | 4 |

The utility of the stabilizer compounds of Examples 1, 2 and 4 in a thermosetting polyester/polyurethane powder coating is demonstrated by the following procedure:

A polyester resin is prepared by heating a mixture of neopentyl glycol (1559 g), trimethylolpropane (100 g) and terephthalic acid (2370 g) in the presence of butyl stannoic acid (3.5 g) at 230° C. for 12–14 hours. The resin has an acid value of 2–5, hydroxyl value of 61, molecular weight (size-exclusion chromatography) of 2400–2600, viscosity (ICI cone and plate, 200° C.) of 12–16 poise and glass-transition temperature of 58°–63° C.

Four powder coating compositions based on the above-described polyester resin are prepared by melt-blending a mixture of:

|  | Weight % |
|---|---|
| Polyester resin | 78.37 |
| Blocked isophorone cross-linking agent | 19.59 |
| Dibutyl tin dilaurate | 0.73 |
| Benzoin | 0.30 |
| Antioxidant | 0.03 |
| Flow control agent | 0.98 |
| Ultraviolet stabilizer compound | x.xx | in a Buss-Kneader PR-46 compounding apparatus at a maximum temperature of 120° C. The four compositions contained respectively the following ultraviolet stabilizers: I—none, II—1.0% Example 1 compound, III—1.0% Example 2 compound and IV—2.0% Example 4 compound. The resulting composition is ground to a fine powder having a maximum particle size of 74 using a cryogenic hammermill and electrostatically applied to zinc-phosphatized, cold-rolled-steel panels at 1.0 to 1.5 mil thicknesses, and finally the coated panels are cured in an oven at 180° C. for 15 minutes. The 60° gloss of the coated panels is measured using a gloss meter (Gardner Laboratory, Inc., Model GC-9095) according to ASTM D-523 both before and after exposing the panels in an accelerated weathering apparatus (Atlas XWR carbon arc Weather-Ometer) for 600, 1000 and 1200 hours. The results are shown below.

| Composition | Gloss at 60° | | | |
|---|---|---|---|---|
|  | Initial | 600 Hrs. | 1000 Hrs. | 1200 Hrs. |
| I | 92 | 86 | 43 | 25 |
| II | 95 | 92 | 65 | 42 |
| III | 94 | 93 | 74 | 54 |
| IV | 93 | 92 | 62 | 38 |

This invention has been described in detail with particular reference to preferred embodiments thereof, but it will be understood that variations and modifications can be effected within the spirit and scope of the invention.

We claim:

1. A compound having the formula

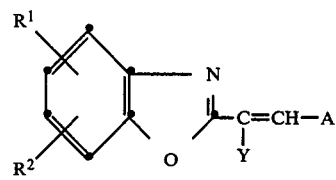

wherein $R^1$ is hydrogen, alkyl, alkoxy or halogen;

$R^2$ is an $R^1$ substituent, carboxyl or alkoxycarbonyl;

Y is carboxyl, alkoxycarbonyl, alkanoyl, cyano, carbamoyl, N-alkylcarbamoyl or N,N-dialkylcarbamoyl; and A is phenyl or phenyl substituted with one or more substituents selected from hydroxy, halogen, alkyl, alkoxy, cycloalkyl, aryl, aryloxy or Y.

2. A compound having the formula

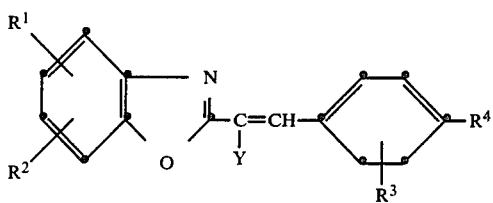

wherein
R¹ is hydrogen, alkyl, alkoxy or halogen;
R² is an R¹ substituent, carboxyl or alkoxycarbonyl; and
R³ and R⁴ are independently selected from hydrogen, alkyl, alkoxy, hydroxy, halogen, cycloalkyl, aryl or aryloxy.

3. A compound having the formula

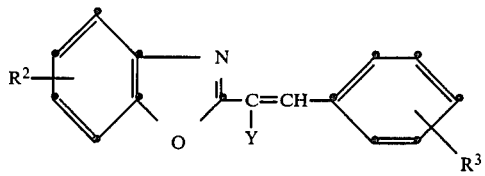

wherein
R² is hydrogen, alkyl, alkoxy, chlorine, carboxyl or alkoxycarbonyl;
Y is alkoxycarbonyl or cyano; and
R³ is ortho or para hydroxy or alkoxy.

4. A compound having the formula

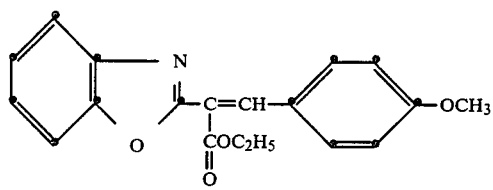

5. A compound having the formula

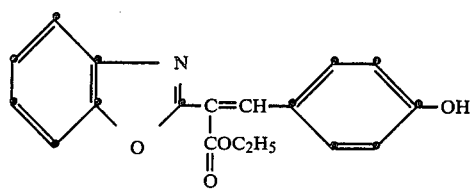

6. A compound having the formula

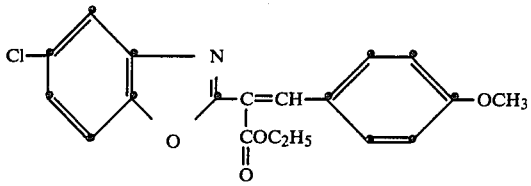

7. A compound having the formula

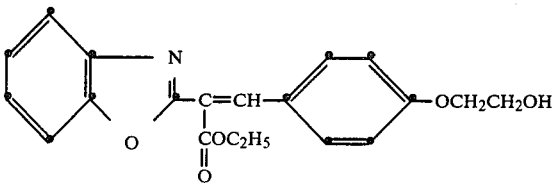

8. A stabilized composition comprising an organic material normally degraded by exposure to ultraviolet light containing a stabilizing amount of a compound having the formula

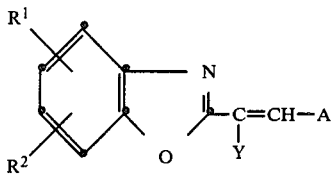

wherein
R¹ is hydrogen, alkyl, alkoxy or halogen;
R² is an R¹ substituent, carboxyl or alkoxycarbonyl;
Y is carboxyl, alkoxycarbonyl, alkanoyl, cyano, carbamoyl, N-alkylcarbamoyl or N,N-dialkylcarbamoyl; and
A is phenyl or phenyl substituted with one or more substituents selected from hydroxy, halogen, alkyl, alkoxy, cycloalkyl, aryl, aryloxy or Y.

9. A stabilized composition according to claim 8 wherein the organic material comprises a polymer containing ester groups.

10. A stabilized polymeric composition comprising a polyester containing recurring phthalate moieties and a stabilizing amount of a compound having the formula

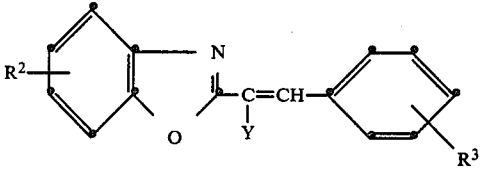

wherein
R² is hydrogen, alkyl, alkoxy, chlorine, carboxyl or alkoxycarbonyl;
Y is alkoxycarbonyl or cyano; and
R³ is ortho or para hydroxy or alkoxy.

* * * * *